United States Patent
Jobling et al.

[11] Patent Number: 6,130,100
[45] Date of Patent: Oct. 10, 2000

[54] MANUFACTURE OF TEST STRIPS

[75] Inventors: Ian Jobling, Bedford; David A. Percival, Harwarden; Michael E. Prior, Northampton, all of United Kingdom

[73] Assignee: Unilever Patent Holdings B.V., Vlaardingen, Netherlands

[21] Appl. No.: 08/935,720

[22] Filed: Sep. 23, 1997

[30] Foreign Application Priority Data

Sep. 27, 1996 [EP] European Pat. Off. ............ 96307088

[51] Int. Cl.[7] .................................................. G01N 33/543
[52] U.S. Cl. ............................. 436/518; 422/56; 422/57; 422/58; 435/4; 435/287.1; 435/287.2; 435/287.7; 435/287.9; 435/805; 435/810; 435/970; 436/169; 436/514; 436/530; 436/810
[58] Field of Search .................... 422/56, 57, 58; 435/4, 287.1, 287.2, 287.7, 287.9, 805, 810, 970; 436/169, 514, 518, 530, 810

[56] References Cited

U.S. PATENT DOCUMENTS 4,235,601  11/1980  Deutsch et al. ........................ 436/805
5,602,040   2/1997  May et al. .............................. 436/514

FOREIGN PATENT DOCUMENTS

WO 95/13542  5/1995  WIPO ........................ G01N 33/558

*Primary Examiner*—Christopher L. Chin
*Attorney, Agent, or Firm*—Pillsbury Madison & Sutro LLP

[57] ABSTRACT

A process of manufacturing test strips of the type comprising a length of porous carrier material capable of acting as a liquid flow path for a sample liquid and having at least zone downstream from a first end of the strip which zone contains an immobilized specific binding agent to act as a capture means during an assay to reveal the presence of an analyte in applied sample liquid, and in which process the specific binding agent is deposited onto a sheet of the porous carrier material which is then blocked and subdivided into a plurality of individual identical test strips, wherein blocking of the porous carrier material is achieved by applying a solution of blocking agent to the sheet upstream from the zone in an amount sufficient to ensure that the solution permeates downstream to beyond the zone. Preferably there is a plurality of zones of immobilized agent arranged in series on the strip, and wherein blocking is achieved by applying a solution of blocking agent to the sheet upstream from the first of the plurality of zones in an amount sufficient to ensure that the solution permeats downstream to beyond the last of the plurality of zones.

13 Claims, 1 Drawing Sheet

MANUFACTURE OF TEST STRIPS

FIELD OF THE INVENTION

This invention relates to improved processes of manufacture of test strips.

BACKGROUND TO THE INVENTION

Simple disposable assay devices, based for example on the technology described in EP-A-291194, are used extensively today in a wide variety of analytical circumstances. These include assays used in the home to detect pregnancy or fertility, and assays used in clinics and doctors offices to detect a wide range of diseases and physiological conditions. Typically these assay devices comprise a dry strip of porous material containing various reagents. The strip can be a single length of material, or can be a composite of various materials arranged in series. A sample liquid is applied to one end of the strip and while it permeates towards the other end, picks up one or more reagents and carries them into a detection zone further along the strip. There may also be a control zone, usually located downstream from the detection zone. Usually the assay result signal and the control signal are created by the accumulation of labelled material in the respective zones. Typically this labelled material comprises a particulate direct label, such as a gold sol or coloured latex micro-particle. Usually the assay strip is protected within a casing, constructed for example from one or more plastics mouldings. However, in some products no casing is provided.

To satisfy the demand for such devices, the test strips must be manufactured in very large numbers. This is achieved by applying to a large sheet or long length of the porous material the various reagents in appropriate locations so that sub-division of the sheet or length into individual identical test strips can be accomplished at a later stage of the manufacturing process. Typically the zone or zones are created by applying appropriate reagents onto the porous carrier by remotely controlled pens or ink-jet printers, which deposit the reagents as lines or as a series of dots. Depending on the reagents used and the nature of the porous carrier material, a chemical pre-treatment procedure may be required. Usually following reagent deposition and drying or fixing, the porous material will need to be "blocked". Mobilisable reagents, such as a labelled reagent deposited elsewhere on the strip, can be applied using similar equipment. A typical manufacturing procedure will therefore entail the bulk portion of porous carrier material being passed through various reagent depositing stations with intermediate stations providing other treatments (eg. blocking) as required. After final drying or other treatment, the porous material is cut or otherwise sub-divided into the individual strips. These procedures can utilise either single large sheets of the porous carrier material or a "continuous" roll. Various lamination or backing materials can also be applied to the porous carrier material while this strip-forming sequence of operations is conducted.

Because such assay strips are required in ever-increasing numbers, there is a need to streamline these operating procedures both to increase throughput and to minimise differences between product batches.

According to one established manufacturing process, in which separate sheets of porous carrier are used, some of the treatments such as blocking are achieved by immersing the whole sheet at an appropriate stage in a bath of blocking solution, followed by draining and drying before further processing. This has the disadvantage that trace amounts of materials can be leached from each sheet upon immersion in the blocking bath. For example, previously deposited reagents may not be completely fixed to the carrier. Moreover, as the blocking agent is progressively consumed during each immersion, the amount of blocking agent applied is not constant. The composition of the blocking solution can therefore change over time, and indeed cause slight contamination of the sheets as leached materials accumulate which may result in a background of non-specific binding when the eventual assay is conducted. Another disadvantage of immersion is that this tends to be a "quick dip", in the interest of manufacturing throughput. However, reagents already deposited in the detection and/or control zones can affect the wetting properties of the porous material at that critical location, and impair the blocking process there, which may lead to variable quality of the signal generated during an eventual assay. A slow blocking procedure, intended to overcome this, introduces delay in the manufacturing process. Similar immersion may form part of a process using a "continuous" long length of carrier material, with comparable disadvantages.

It is desirable to ensure that previously deposited reagents on the carrier material are not dislodged by later processing steps and relocated in regions of the strip wherein non-specific binding could be disadvantageous during use.

It is therefore an object of the invention to provide a manufacturing process for assay strips which especially enables blocking of the strip material to be accomplished more readily and without significant potential disruption to the final assay performance.

GENERAL DESCRIPTION OF THE INVENTION

The invention provides a process of manufacturing test strips of the type comprising a length of porous carrier material capable of acting as a liquid flow path for a sample liquid and having at least one zone downstream from a first end of the strip which zone contains an immobilised specific binding agent to act as a capture means during an assay to reveal the presence of an analyte in applied sample liquid, and in which process the specific binding agent is deposited onto a sheet of the porous carrier material which is blocked and subdivided into a plurality of individual identical test strips, wherein blocking of the porous carrier material is achieved by applying a solution of blocking agent to the sheet upstream from the zone in an amount sufficient to ensure that the solution permeates downstream to beyond the zone.

Preferably there is a plurality of zones of immobilised agent arranged in series on each strip, and blocking is achieved by applying a solution of blocking agent to the sheet upstream from the first of the plurality of zones in an amount sufficient to ensure that the solution permeates downstream to beyond the last of the plurality of zones.

Preferably the zones include at least one test zone to reveal the presence of the analyte, and a control zone downstream from the test zone which control zone contains an immobilised specific binding agent to act as a capture means during the generation of a control signal during the assay, and the specific binding agent in the control zone does not bind the specific binding agent in the test zone.

Preferably the porous carrier material is nitrocellulose, more preferably backed with plastics sheet material such as polyester. However, other carrier materials, such as paper, as conventionally used in assay strips, are suitable.

Conveniently, the blocking agent solution is applied at or near the edge of the sheet which constitutes the first ends of the strips after subdivision.

Where a plurality of zones of immobilised reagent occur, the reagent can be the same or different in each or several of the zones, depending on the type of assay result required. For example, this may be a simultaneous test for two or more analytes in a single sample liquid. Each specific binding agent can be deposited as a line of reagent which, after subdivision of the sheet into individual assay strips, lies across the width of each strip. The line may be continuous, or composed of a series of individual dots or geometric shapes or patterns.

The blocking agent can be non-specific protein, preferably an albumin such as bovine serum albumin. Alternatively, the blocking agent is a polyvinyl alcohol. If desired the blocking agent may be applied in a buffered solution; an aqueous Tris buffer is ideal. Especially for use with a nitrocellulose carrier, an ideal blocking solution is an aqueous Tris buffer containing PVA. Optionally, a wetting agent, such as detergent or an alcohol, especially ethanol, can be included, as this improves flow of the applied solution.

Preferably, the specific binding agent immobilised in the test zone is an antibody raised in a first species and the specific binding reagent immobilised in the control zone is an antibody raised against an antibody from a species different from the first species.

The invention will be described with particular reference to test strips useful in monitoring of body fluid analytes, and especially to home monitoring of urinary analytes of relevance to the determination of pregnancy (hCG) or of the fertility status of the human ovulation cycle (for example LH and/or E3G and/or P3G). This is by way of example only, and it will be appreciated that the invention is useful in many other contexts where other sample liquids and analytes are involved. Examples of other types of analyses in which a test strip in accordance with the invention may be appropriate include assays for cancer markers, cardiac markers, blood glucose, drugs of abuse, hormones, infectious disease markers, tests in therapeutic drug monitoring, manufacturing and raw material quality control, and tests for effluent and pollution levels.

BRIEF DESCRIPTION OF THE DRAWINGS

By way of example only, an embodiment of the invention will now be described with reference to the accompanying drawings, which are provided for the purposes of general illustration only and are not to scale.

FIGS. 3a and 3b show the differing consequences of using alternative reagents on the sheet, as described herein.

DETAILED DESCRIPTION OF THE INVENTION

Figure 1:
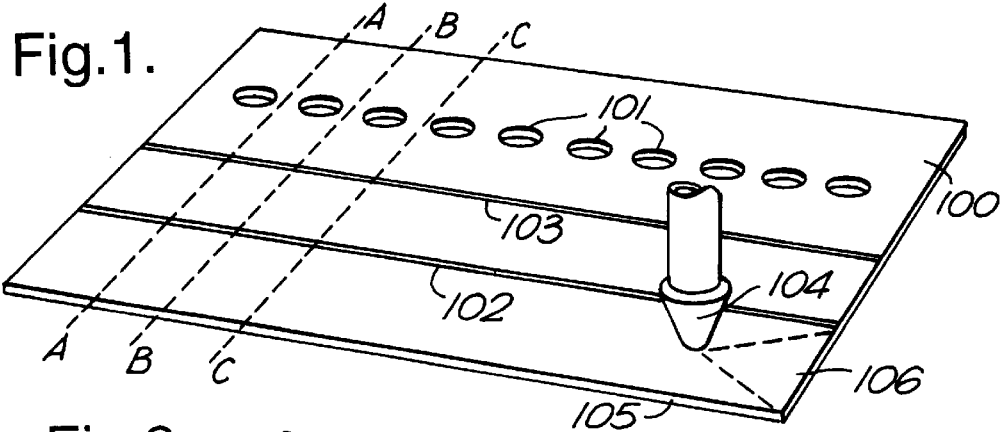
FIG. 1 depicts a general view of a sheet of porous carrier material being traversed by a nozzle applying blocking solution to the sheet.

Referring to FIG. 1 the sheet 100 of porous material, for example polyester-backed nitrocellulose having a pore size of about 8 microns, is depicted as being rectangular. At a subsequent stage in a manufacturing process sheet 100 will be subdivided, for example by cutting, to provide a plurality of identical test strips. Lines AA, BB and CC in FIG. 1 represent lines along which such cutting will occur. As shown, a single assay strip occupies the entire front-to-back depth of sheet 100. Alternative geometric layouts can be chosen. For the purposes of illustration only the following description will assume that individual large sheets of the porous material are being processed. However, the principles of the invention apply equally well to "continuous" manufacturing processes in which sheet 100 as seen in FIG. 1 is merely part of a very long length of porous material being fed into the process from a reel for example.

Sheet 100 has a plurality of holes 101 perforating it and running in a line parallel to the longer dimension of the sheet and lying towards the rear (downstream end) of the sheet. When sheet 100 is subdivided into assay strips, each strip will include one of these holes. These holes can provide a registration means to facilitate progress of the sheet through the manufacturing process and to act as a guide for accurate and consistent deposition of reagents on the sheet. Subsequently, if desired, the registration hole in an individual strip can be used to ensure accurate location of the strip within an assay device. These features are described in detail in EP-A-728309.

At an earlier stage in the manufacturing process, two parallel lines 102 and 103 of specific binding reagent have been deposited on the sheet, also running parallel to the longer dimension. These lines constitute respectively a test zone (102) and a control zone (103) in the individual test strips. At the stage depicted in FIG. 1, these lines of specific binding reagents have been deposited and fixed as appropriate, so that in principle these reagents do not migrate within the porous sheet material when wet. The practical reality may be different however, as is described below.

The manufacturing stage depicted in FIG. 1 is the deposition of a liquid reagent, for example a blocking solution on the sheet. Sheet 100 is lying essentially horizontal. A nozzle 104 (the details of which are not critical to the invention) is just starting a traverse from right to left across the sheet, parallel to and close to the front edge 105. For these purposes it is immaterial whether the nozzle moves relative to a stationary sheet, or whether the nozzle is fixed and the sheet is moving. A region 106 of applied liquid from the nozzle is forming on the sheet and spreading outwardly from the line of travel of the nozzle by capillary action.

Figure 2:
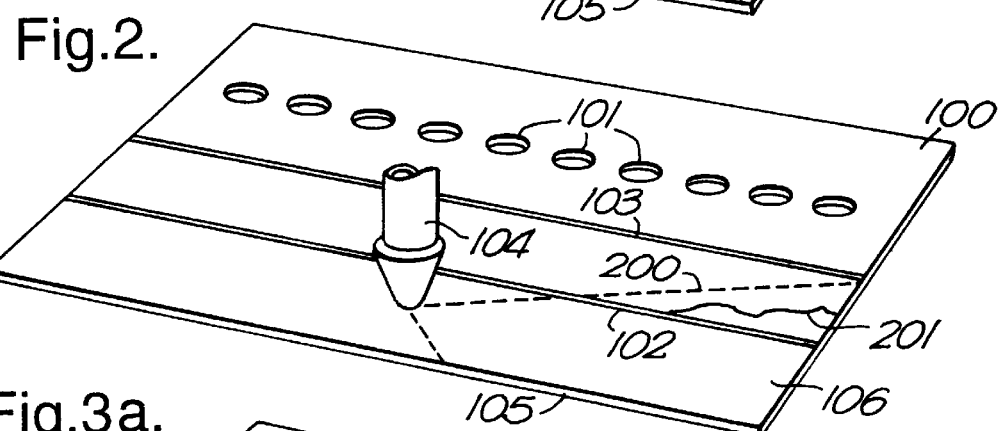
FIG. 2 shows the same sheet with the nozzle further advanced across the sheet.

FIG. 2 shows nozzle 104 about half way across sheet 100. The region 106 moistened by the applied solution is obviously increasing. It is constrained by the adjacent front edge 105 of sheet 100, but the applied liquid can permeate progressively towards the rear of the sheet. Broken line 200 represents the extent of this liquid movement. This solvent front has crossed line 102 of deposited reagent constituting the detection zone, but has not yet reached line 103. A small proportion of the deposited reagent in line 102 has not been effectively immobilised at that location and has begun to migrate out of line 102 under the influence of the diffusing liquid. The extent of this migration is represented by line 201.

Figure 3A:
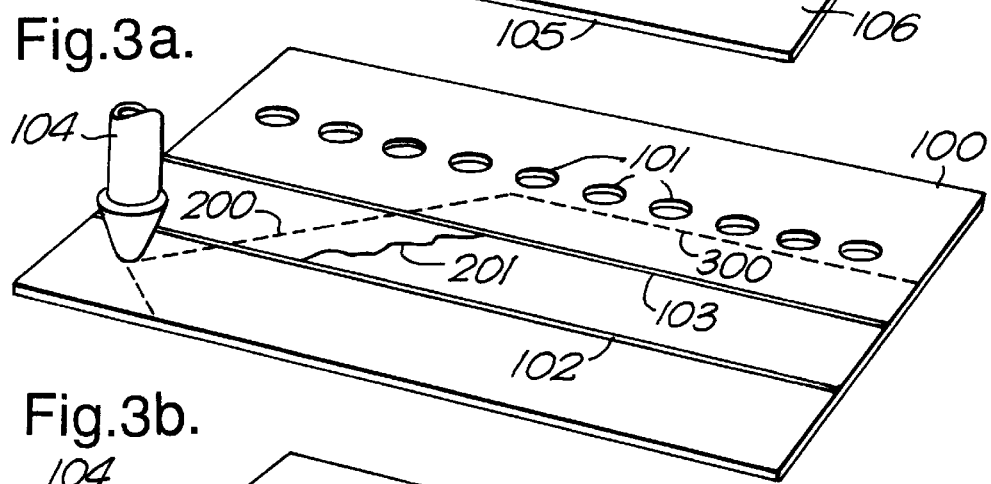
FIGS. 3a and 3b both show the same sheet with the nozzle almost fully advanced across the sheet.

Referring to FIG. 3a, nozzle 104 has almost completely traversed sheet 100. The region 106 of the sheet moistened by the sprayed solution is obviously greater, and towards the right hand side of the sheet the solvent front 300 has reached an equilibrium point and is now stationary. Stationary front 300 is beyond control line 103 but in front on the perforations 101. For the purposes of this description the exact position of this stationary front is not of consequence, provided it is significantly beyond the control line. Migration of unbound reagent from test line 102 is depicted by line 201. In the version as shown in FIG. 3a, the immobilised reagent in control line 103 is capable of binding to the reagent in test line 102 and accordingly migration of unbound reagent from test line 102 has ceased when this reagent has reached the control line. This would occur, for example, if the test line reagent is a murine monoclonal antibody and the control line comprises an immobilised "anti-mouse" antibody. In such an instance, the effectiveness of the control line during a subsequent assay could be reduced because some of its binding capability has already been taken up by unbound reagent migrating from the test line. If a proportion of the reagent originally deposited in control line 103 has also not been effectively immobilised at that location, it may also migrate downstream from these towards the rear of sheet 100, but this has not been shown.

Figure 3B:
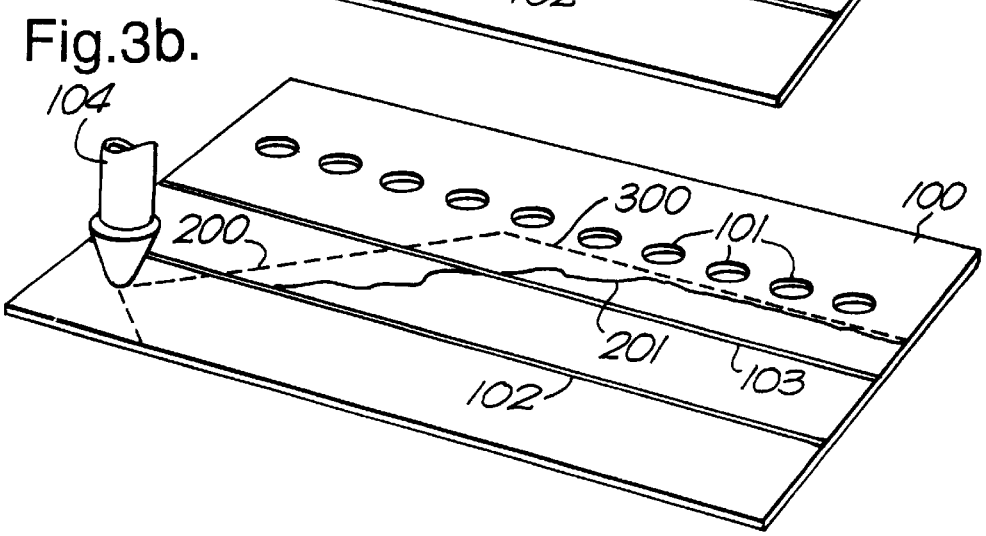

A similar situation is shown in FIG. 3b, but in this instance there is negligible cross-reactivity between the different reagents deposited in test line 102 and control line 103. This is a preferred embodiment. The extent of migration of unbound reagent from the test line is again shown (line 200) but this now extends beyond control line 103 and eventually up to the stationary solvent front 300. As before, unbound control-line reagent may also migrate downstream.

If a sufficient quantity of blocking solution is applied along the front edge of the sheet, this permeation of liquid through the test and control lines can effectively wash unbound reagents from both lines towards the back of the sheet and away from the region, containing the test and control lines, of the assay strip which needs to be viewed by a user of the eventual test.

If desired, the blocking solution can optionally include other reagents, e.g. sugar such as sucrose to promote reagent stability during storage of the manufactured strip.

As a further alternative, such optional reagents can be applied subsequently to the strip. In any event, it may be beneficial to apply a water wash to the strip, again by means of a traversing nozzle near the upstream edge of the sheet, to wash excess blocking agent towards the downstream edge. Such optional reagents can be introduced during such a wash step.

EXAMPLE

This example is described in relation to the blocking of a sheet of nitrocellulose carrier of pore size about 8 microns cast onto a backing sheet of "Mylar" polyester. The sheet is rectangular and has a length of 250 millimetres and a front-to-back width of 40 millimetres which is the intended length of an individual assay strip to be subdivided from the sheet. Each strip would have a width of about 5 millimetres. Two lines of antibody reagent have already been deposited along the entire length of the sheet using conventional reagent deposition technology such as a pen and an "XY" plotting mechanism. A first line runs parallel to the front edge of the sheet and is 8 millimetres away from the edge. This line contains a conventional murine anti-β hCG monoclonal antibody deposited on the sheet as a 2.5 mg/ml solution. The second line is parallel to the first and is 16 millimetres from the front edge of the sheet. This is a control line containing a monoclonal or polyclonal antibody raised against rabbit IgG. This antibody has also been deposited as a 2.5 mg/ml solution. After deposition these reagent lines have been "fixed" by drying using warm air. The invention is concerned with the subsequent blocking of this pre-treated sheet.

A blocking solution is prepared as follows. 400 ml of an aqueous solution contains the following ingredients:

| 2.42 gm | Tris |
|---------|------|
| 0.5 gm | Tween 20 |
| 8.76 gm | Sodium chloride |
| 10 gm | PVA |

To this is added 50 ml of ethanol and the pH is adjusted to 7.4 by the addition of hydrochloric acid. Further water is added to make the total volume 1 liter. This solution therefore contains about 1% of the PVA blocking agent.

This blocking solution is applied to the pretreated sheet using a nozzle which tracks across the front of the sheet at a rate of 10 cm per second along a line about 4 millimetres in from the front edge of the sheet. By simple experiment the amount of blocking agent metered onto the sheet during this passage of the nozzle is adjusted so that the applied blocking solution migrates towards the back edge of the sheet to an extent which is beyond the control line. The actual quantity of blocking solution required obviously varies according to a number of factors including the thickness and batch characteristics of the nitrocellulose, and the ambient conditions which may affect the rate of evaporation of the blocking solution and hence the position of the final solvent front. Adjustment of the quantity of applied liquid is easily made using conventional metered pump technology.

Following application of the blocking solution the moist sheet should be dried in a controlled manner, for example, using warm air to achieve uniform drying across the sheet.

Other components such as sucrose can be added to the blocking solution. Alternatively, prior to drying of the sheet after blocking, a second liquid application can be made using for example an aqueous solution of sucrose containing about 20 grams per liter. This can be applied using a similar nozzle and metering system. Application of the sucrose solution is along the same line as the blocking solution eg. about 4 millimetres from the front edge of the sheet. In this optional arrangement it is best if the quantity of blocking solution applied is just sufficient to take the solvent front up to or just beyond the control line. The quantity of sucrose solution applied should be sufficient to carry the sucrose at least as far as the control line. This will flush the blocking solution towards the back edge of the sheet.

After drying and such other processing as may be required, eg. the deposition of a mobilisable labelled reagent near the front edge of the sheet and any final drying of preservation treatment that may be required, the sheet is divided into individual assay strips which can be incorporated in assay devices. Preferably any labelled component is contained in a separate pad of porous material which is located upstream from the strip in an assay device. The constructional details of assay devices in which the test strips of the invention can beneficially be incorporated are described in numerous publications, for example, EP-A-291194, EP-A-383619, WO 96/09553 and WO 96/09546.

What is claimed is:

1. In a process of manufacturing test strips of the type comprising a length of porous carrier material capable of acting as a liquid flow path for a sample liquid and having at least one zone downstream from a first end of said strip which zone contains an immobilised specific binding agent to act as a capture means during an assay to reveal the presence of an analyte in applied sample liquid, the improvement wherein the process comprises the steps of depositing said specific binding agent onto a sheet of said porous carrier material followed by blocking and then subdividing the blocked sheet into a plurality of individual identical test strips, the blocking of said porous carrier material being achieved by applying a solution of blocking agent to said sheet upstream from said zone in an amount sufficient to ensure that said solution permeates downstream to beyond said zone to effect said blocking.

2. A process according to claim 1, wherein said porous carrier material is nitrocellulose.

3. A process according to claim 2, wherein said nitrocellulose is backed with plastics sheet material.

4. A process according to claim 3, wherein said plastics sheet material is polyester.

5. A process according to claim 1, wherein said blocking agent solution is applied at or near the edge of the sheet which constitutes the first ends of said strips after subdivision.

6. A process according to claim 1, wherein said specific binding agent is deposited as a line of reagent across the width of said sheet.

7. A process according to claim 1, wherein said blocking agent is a non-specific protein.

8. A process according to claim 7, wherein said non-specific protein is an albumin.

9. A process according to claim 8, wherein said albumin is bovine serum albumin.

10. A process according to claim 1, where in said blocking agent is polyvinyl alcohol.

11. A process according to claim 1, wherein there is a plurality of zone of immobilised agent arranged in series on said strip, and wherein blocking is achieved by applying a solution of blocking agent to said sheet upstream from the first of said plurality of zones in an amount sufficient to ensure that said solution permeates downstream to beyond the last of said plurality of zones.

12. A process according to claim 11, wherein said zones include at least one test zone to reveal the presence of said analyte, and a control zone downstream from said test zone which control zone contains an immobilised specific binding agent to act as a capture means during the generation of a control signal during said assay, and said specific binding agent in said control zone does not bind said specific binding agent in said test zone.

13. A process according to claim 12, wherein said specific binding agent immobilised in said test zone is an antibody raised in a first species and said specific binding reagent immobilised in said control zone is an antibody raised against an antibody from a species different from said first species.

* * * * *